(12) United States Patent
Biedermann et al.

(10) Patent No.: US 9,198,702 B2
(45) Date of Patent: Dec. 1, 2015

(54) BONE SCREW

(75) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 553 days.

(21) Appl. No.: 13/034,574

(22) Filed: Feb. 24, 2011

(65) Prior Publication Data

US 2011/0213423 A1 Sep. 1, 2011

(30) Foreign Application Priority Data

Feb. 26, 2010 (EP) ..................................... 10154810

(51) Int. Cl.
 *A61B 17/86* (2006.01)
(52) U.S. Cl.
 CPC ............ *A61B 17/864* (2013.01); *A61B 17/8625* (2013.01); *A61B 17/866* (2013.01); *A61B 17/8635* (2013.01)
(58) Field of Classification Search
 CPC .... A61B 17/84; A61B 17/86; A61B 17/8605; A61B 17/8625; A61B 17/863; A61B 17/8635; A61B 17/864; A61B 17/8645; A61B 17/866
 USPC .................... 606/301–321; 411/82, 82.1, 395
 See application file for complete search history.

(56) References Cited

U.S. PATENT DOCUMENTS

| | | | |
|---|---|---|---|
| 3,115,804 A | 12/1963 | Johnson | |
| 3,467,209 A | 9/1969 | Chromy | |
| 4,484,570 A * | 11/1984 | Sutter et al. | 606/282 |
| 4,537,185 A * | 8/1985 | Stednitz | 606/304 |
| 5,713,902 A | 2/1998 | Friedl | |
| 5,964,767 A | 10/1999 | Tapia et al. | |
| 6,120,511 A | 9/2000 | Chan | |
| 6,283,973 B1 * | 9/2001 | Hubbard et al. | 606/104 |
| 6,500,205 B1 * | 12/2002 | Michelson | 623/17.16 |
| 6,508,818 B2 | 1/2003 | Steiner et al. | |
| 6,565,572 B2 | 5/2003 | Chappius | |

(Continued)

FOREIGN PATENT DOCUMENTS

| | | |
|---|---|---|
| DE | 299 14 192 U1 | 11/1999 |
| EP | 1 093 773 A1 | 4/2001 |

(Continued)

OTHER PUBLICATIONS

Extended European Search Report dated May 17, 2010 for Application EP 10 15 4810, 6 sheets.

(Continued)

*Primary Examiner* — Christian Sevilla
*Assistant Examiner* — Eric S Gibson
(74) *Attorney, Agent, or Firm* — Christie, Parker & Hale, LLP

(57) ABSTRACT

A bone screw is provided that includes a tubular body having a first end and a closed second end. The tubular body has a tubular wall defining a cavity wherein the thickness of the wall in a radial direction is smaller than an inner radius of the cavity and wherein a plurality of recesses is provided extending entirely through the tubular wall into the cavity. The tubular body further includes an exterior bone thread on an exterior tubular surface portion of the tubular wall, a head at the first end configured to engage with a driver to advance the bone screw in the bone, and a tip at the second end. The tubular body, the head and the tip are formed as a single piece.

13 Claims, 2 Drawing Sheets

(56) References Cited

U.S. PATENT DOCUMENTS

| | | | |
|---|---|---|---|
| 6,755,835 B2* | 6/2004 | Schultheiss et al. | 606/304 |
| 6,863,671 B1 | 3/2005 | Strobel et al. | |
| 7,172,595 B1 | 2/2007 | Goble | |
| 7,261,716 B2* | 8/2007 | Strobel et al. | 606/314 |
| 7,938,831 B2* | 5/2011 | Leroux et al. | 606/86 R |
| 2001/0007072 A1 | 7/2001 | Steiner et al. | |
| 2004/0015172 A1 | 1/2004 | Biedermann et al. | |
| 2004/0068261 A1 | 4/2004 | Fourcault et al. | |
| 2004/0122431 A1* | 6/2004 | Biedermann et al. | 606/73 |
| 2004/0122432 A1 | 6/2004 | Chappuis | |
| 2004/0147929 A1 | 7/2004 | Biedermann et al. | |
| 2004/0225292 A1* | 11/2004 | Sasso et al. | 606/73 |
| 2006/0247642 A1* | 11/2006 | Stone et al. | 606/73 |
| 2007/0025827 A1 | 2/2007 | Pryor | |
| 2008/0004627 A1 | 1/2008 | Dalton | |
| 2008/0039846 A1 | 2/2008 | Lee et al. | |
| 2008/0161864 A1* | 7/2008 | Beck et al. | 606/326 |
| 2008/0306601 A1* | 12/2008 | Dreyfuss | 623/19.14 |
| 2009/0018590 A1 | 1/2009 | Dorawa et al. | |
| 2009/0248089 A1 | 10/2009 | Jacofsky et al. | |
| 2009/0318981 A1* | 12/2009 | Kang | 606/329 |
| 2010/0298889 A1 | 11/2010 | Wilberg et al. | |
| 2011/0060373 A1* | 3/2011 | Russell et al. | 606/304 |
| 2011/0137352 A1 | 6/2011 | Biedermann et al. | |

FOREIGN PATENT DOCUMENTS

| | | |
|---|---|---|
| EP | 2 140 824 A1 | 1/2010 |
| GB | 2 417 536 A | 3/2006 |
| JP | 09-509333 A | 9/1997 |
| WO | WO 97/25939 | 7/1997 |
| WO | WO 01/26568 A1 | 4/2001 |
| WO | WO 01/76494 A1 | 10/2001 |
| WO | WO 03/068048 A2 | 8/2003 |
| WO | WO 2006/031397 A1 | 3/2006 |
| WO | WO 2007/124253 A2 | 11/2007 |

OTHER PUBLICATIONS

Extended European Search Report for Application No. EP 13 19 9316, dated Feb. 20, 2014, 8 pages.

Office action for U.S. Appl. No. 12/958,914 dated Oct. 9, 2012 (17 pages).

Final Rejection for U.S. Appl. No. 12/958,914 dated May 9, 2013 (16 pages).

Office action for U.S. Appl. No. 12/958,914 dated Aug. 1, 2014 (20 pages).

Final Rejection for U.S. Appl. No. 12/958,914 dated Jun. 2, 2015 (31 pages).

* cited by examiner

BONE SCREW

CROSS-REFERENCE TO RELATED APPLICATIONS

This Application claims priority to and the benefit of U.S. Provisional Application No. 61/308,464, filed Feb. 26, 2010, the entire contents of which are incorporated herein by reference. This Application also claims priority to and the benefit of EP 10 154 810.5, filed in the European Patent Office on Feb. 26, 2010, the entire contents of which are incorporated herein by reference.

BACKGROUND

The invention relates to a bone screw. In particular, the invention relates to a bone screw that can be used as an anchor screw and a fusion screw that fuses with the surrounding bone material.

A bone screw that can be used as a fusion screw is known from U.S. 2004/0015172 A1. This bone screw has a tubular thread section with a bone thread and with a plurality of recesses in its wall, and a head and a tip that can be connected to the tubular thread section. In use, the tubular portion can be filled with bone material or other growth promoting material and then the tip and/or the head are connected to the tubular portion. Usually the screw is inserted into a core hole in the bone that is prepared in advance. After insertion of the screw into the bone, fusion of the screw with the surrounding bone material takes place. The screw can act as a traction element to connect shattered or split off parts of bones together by means of the screw.

SUMMARY

It is the object of the invention to provide an improved bone screw of the afore-mentioned type, the position of which in the bone can be corrected after insertion and which can be easily removed later, if required.

The bone screw according to the invention is fellable with a substance to support fusion and is precisely positionable. When the bone screw is inserted into a core hole that has been prepared in advance, the bone thread at the exterior wall surface engages the bone, and the screw is advanced by screwing it deeper into the bone by means of a screw driver. To adjust the position of the bone screw, it might be necessary to screw it back to reposition the screw. This is facilitated, since the head and the tubular body of the bone screw are firmly connected without a risk of loosening or disconnection.

The bone screw can act as a bone anchor or can be used to connect broken elements of bones or as a support beam to strengthen weak bones.

In certain situations, it might be clinically necessary to remove an implanted bone screw at a later stage, when it may have already fused with the surrounding bone material. Since the head and the tubular body are integrally formed, it is possible to remove a bone screw that already has fused with the surrounding bone material.

Further features and advantages of the invention will become apparent from the description of embodiments of the invention by means of the accompanying drawings.

DETAILED DESCRIPTION

Figure 1:
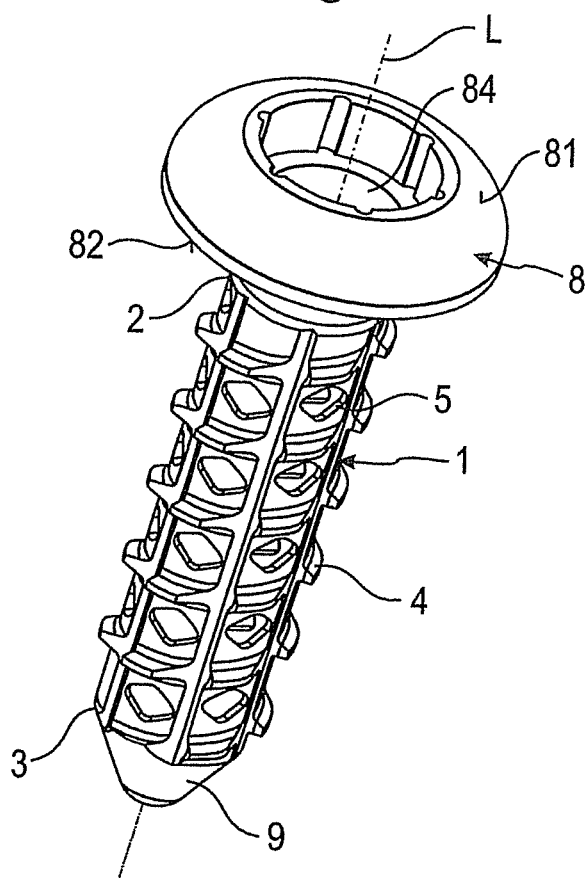
FIG. 1 shows a perspective exploded view of a bone screw according to a first embodiment.
Figure 2:
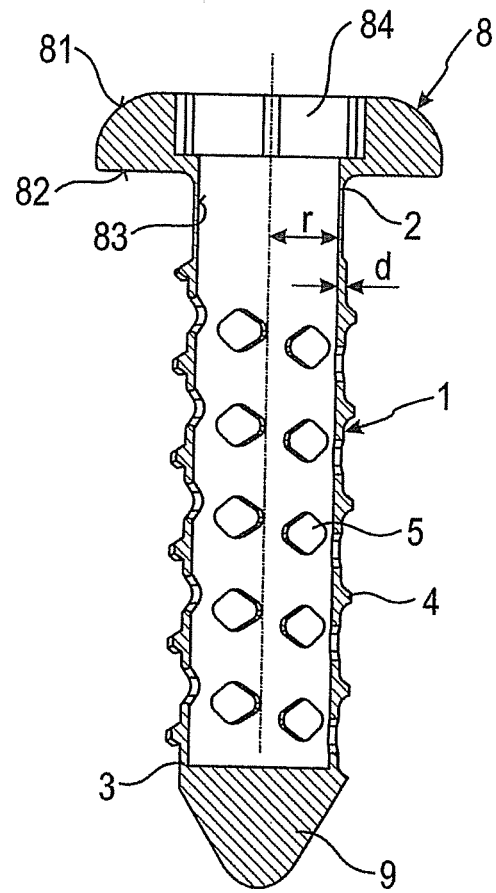
FIG. 2 shows a cross-sectional side view of the bone screw of FIG. 1, the section being taken along the screw axis.
Figure 3:
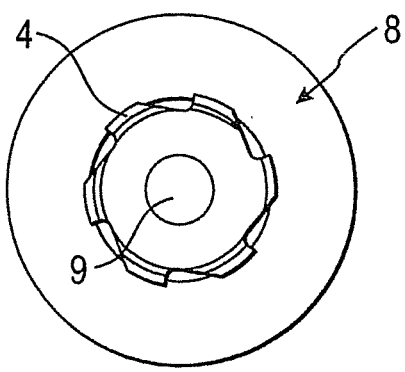
FIG. 3 shows a bottom view of the bone screw of FIG. 1.

The bone screw according to an embodiment as shown in FIGS. 1 to 3 comprises a tubular body 1 with a first end 2, a second end 3 and a screw axis L. The tubular body is substantially cylindrical. It has a tubular wall defining a cavity. On the exterior surface of the tubular wall, a so-called bone thread 4 is provided. In the embodiment as shown, the bone thread 4 is provided along the whole length of the tubular body 1. The bone thread 4 is configured to cut into the bone when the bone screw is screwed-in to the bone. Further, a plurality of openings 5 are located in the tubular wall, which extend entirely through the tubular wall into the cavity. The openings 5 are shown as diamond-shaped and are located between the crests of the bone thread 4. However, any other variation of the shapes and locations of the openings 5 are conceivable.

The cavity provided by the tubular body 1 has a volume that is suitable for accommodating bone material, for example bone chips. The wall thickness d of the tubular body 1 is smaller than an inner radius r of the cavity formed by the tubular body. More preferably, the wall thickness d of the tubular body is smaller than about 15% of the outer diameter of the tubular body.

Adjacent the first end 2, a head 8 is formed in one piece with the tubular body 1. Adjacent the second end 3, a tip 9 is formed in one piece with the tubular body 1. As a result thereof, the bone screw is a one-piece screw. The head 8 has a largest outer diameter that is larger than the outer diameter of the bone thread of the tubular body 1. As seen in particular in FIG. 2, the head 8 has an upper side 81 facing away from the tubular body 1 and a lower side 82 facing the tubular body 1. A surface of the upper side 81 can be lens-shaped, dome-shaped, flat or otherwise shaped. The surface of the lower side 82 comprises a flat portion for abutment against the bone surface. In the embodiment shown the whole lower side 82 is flat.

A coaxial bore 83 extends from the upper side 81 to the lower side 82 and is continuous with the cavity formed by the tubular body 1. Further, a recess 84 is provided at the upper side 81 for engagement with a screw-driver. In the embodiment shown, the recess is star-shaped. However, it can have any other suitable shape, such as a hexagon or other polygon shape that allows a form-fit engagement with a screw-driver. The inner diameter of the recess 84 is larger than the inner diameter of the coaxial bore 83. It is possible to fill the bone screw with bone chips or other bone materials through the recess 84 and the coaxial bore 83 since the size of coaxial bore 83 is large enough to allow the introduction of small bone parts.

The tip 9 is formed as a solid tip without a channel extending therethrough.

The bone screw is made of a body-compatible material, such as a body-compatible metal, for example stainless steel or titanium; a body-compatible metal alloy, for example a Ni—Ti-alloy such as Nitinol; or made of a body-compatible plastic material, for example PEEK.

The tubular body or other parts of the bone screw can be coated with an in-growth promoting material or can be roughened to enhance in-growth of bone or vessels.

In use, first, bone chips are filled into the cavity provided by the tubular body 1. The thus prepared bone screw can then be inserted into a core hole in the bone that has been prepared in advance. Slight corrections of the position of the bone screw in the core hole can be made by rotating the screw-driver in the reverse direction, so that the screw is screwed back. In some clinical applications the bone screw is used as compression screw that connects broken bone fragments by compressing them. The flat surface provided at the lower side acts as an abutment against the bone surface. After a certain time, fusion of the surrounding bone with the bone screw takes place. It is possible to remove an implanted bone screw at a later stage when it may have already fused with its surrounding bone material.

A kit of several bone screws with different volumes of the cavity, a different diameter and different lengths can be provided. The surgeon selects the appropriate bone screw and fills it with bone material and inserts it into the bone. Since the bone screw is a single piece it is simple to handle.

Figure 4:
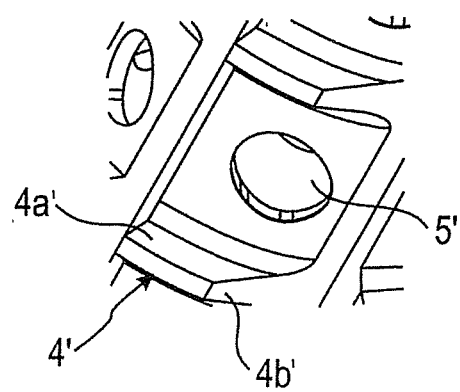
FIG. 4 shows an enlarged portion of the tubular body of the bone screw of FIG. 1 in a modified example of the openings in the wall.

A modification of the bone thread is shown in FIG. 4. The crests 4' of the bone thread are interrupted at regular distances, i.e. crest portions 4a' are arranged on a helical line around the exterior wall surface of the tubular body 1. The crest portions may have inclined surfaces 4b' extending in the direction of the helix and in a reverse direction. The openings 5' are oval-shaped.

Figure 5:
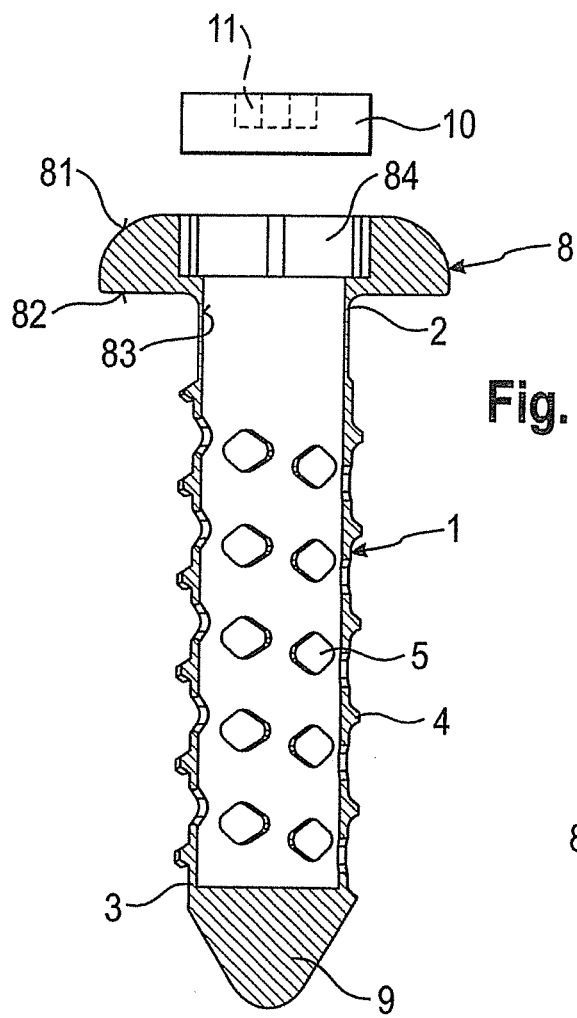
FIG. 5 shows a sectional view of a bone screw of FIG. 1 in a modified embodiment.

Furthermore, a modified embodiment is shown in FIG. 5. The modified embodiment of the bone screw differs from the embodiment shown in FIGS. 1 to 3 in that additionally a plug member 10 is provided for closing the cavity at the side of the head 8. The plug member 10 has a contour and a size that fits into the recess 84 so that the bore 83 and therefore the cavity is closed. The plug member 10 can have an engagement portion 11 for engagement with a screw-driver or a holding instrument.

In use, the plug member 10 can be inserted after filling the cavity with bone material and before inserting the bone screw into the core hole. Alternatively, the plug member can be inserted after the bone screw has been inserted into the core hole and brought to its final position.

Figure 6:
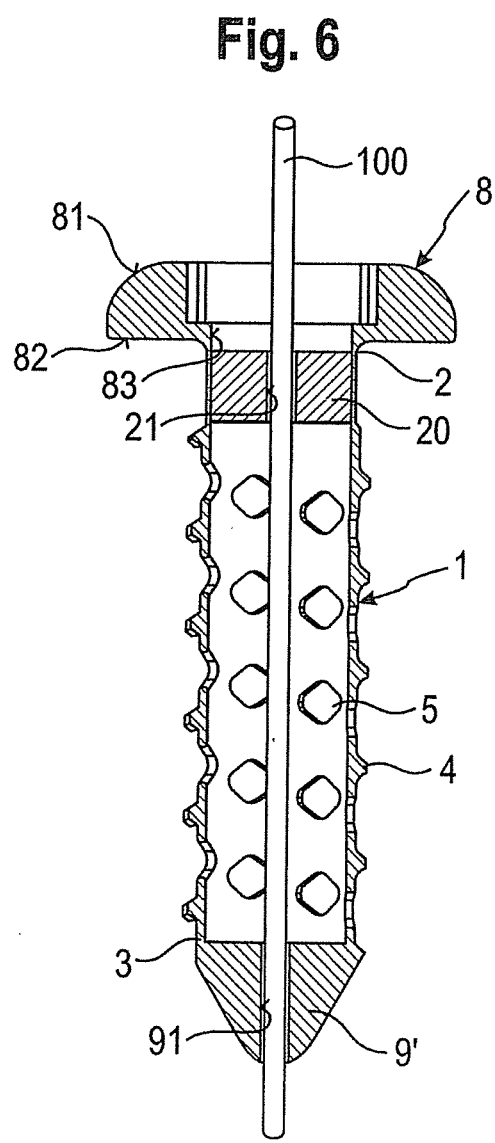
FIG. 6 shows a sectional view of a bone screw of FIG. 1 in a further modified embodiment.

A further modified embodiment is shown in FIG. 6. The bone screw according to the modified embodiment has a cannulated tip 9' with a channel 91 that has a size such that a guide wire 100 can be guided therethrough. Further, a guide member 20 can be provided, which is insertable into the tubular body. The guide member 20 can be a plug-like member that is sized such that the plug member 20 is held mainly by friction within the tubular body 1. The guide member 20 has a coaxial bore 21 that is sized such that the guide wire 100 can be passed therethrough and is guided by the guide member 20.

In a still further modified embodiment, instead of the guide member 20, the plug member 10 shown in FIG. 5 comprises a coaxial bore for guiding the guide wire 100 therethrough.

The modified embodiment that can be used with a guide wire is particularly applied in minimally invasive surgery ("MIS"). In this case, the guide wire is introduced through the skin of the patient and advanced through the tissue until it reaches the position where the bone screw is to be placed. The guide wire is inserted into the bone to the appropriate direction and depth. The bone screw is then guided along the guide wire extending therethrough until it reaches the surface of the bone and then screwed into the bone guided by the guide wire.

Further modifications of the bone screw are possible. For example, the tip can be formed as a self-cutting tip that is configured to cut the bone.

The head 8 can have a largest outer diameter that is equal to or smaller than the largest outer diameter of the tubular body 1 so that the bone screw can be immersed into the bone to a certain depth without any portion of the bone screw projecting above the surface of the bone.

What is claimed is:

1. A bone screw comprising:
    a tubular body having a longitudinal axis and a first end and a second end at opposite ends of said longitudinal axis, wherein the tubular body has a tubular wall defining a thickness and a cavity, wherein the thickness of the wall in a radial direction is smaller than an inner radius of the cavity and wherein a plurality of recesses are provided extending entirely through the tubular wall into the cavity;
    an exterior bone thread on an exterior tubular surface portion of the tubular wall, the exterior bone thread having interrupted crests;
    a head at the first end configured to engage with a driver to advance the bone screw in a bone; and
    a tip at the second end; and
    wherein the tubular body, the head and the tip are formed as a monolithic piece;
    wherein the interrupted crests define gaps in the exterior bone thread, wherein the gaps are along a line directed along the longitudinal axis of the tubular body and wherein a solid portion of said tubular wall remains radially below each gap of said gaps; and
    wherein at least two recesses of the plurality of recesses are located adjacent to and on opposite sides of the line.

2. The bone screw of claim 1, wherein the head has a coaxial bore with a diameter equal to or larger than an inner diameter of the tubular body at the first end.

3. The bone screw of claim 2, further comprising a plug member insertable into the bore for closing the bore.

4. The bone screw of claim 1, wherein the head has a largest outer diameter that is larger than an outer diameter of the tubular body.

5. The bone screw of claim 1, wherein the head comprises a flat surface portion facing in a direction towards the second end of the tubular body.

6. The bone screw of claim 1, wherein the head has a recess on its upper side facing away from the second end of the tubular body, the recess having a structure to provide form-fit engagement with the driver.

7. The bone screw of claim 1, wherein the bone thread extends along an entire length of the exterior tubular surface of the tubular wall.

8. The bone screw of claim 1, wherein the tubular body is cylindrical.

9. The bone screw of claim 1, wherein the tip is configured to close the tubular body at the second end.

10. The bone screw of claim 1, wherein the line is straight.

11. The bone screw of claim 1, wherein the two recesses are on opposite sides of the line at a first axial circumference along the longitudinal axis of the tubular body.

12. The bone screw of claim 11, wherein the plurality of recesses comprises two additional recesses located adjacent to and on opposite sides of the line at a second axial circumference along the longitudinal axis of the tubular body, wherein the second axial circumference is above or below the first axial circumference.

13. The bone screw of claim 1, wherein the interrupted crests comprise inclined surfaces along a direction of the helix of the bone thread, the inclined surfaces defining opposite sides of each of the gaps, wherein, at each gap, the inclined surfaces on opposite sides of each gap radiate from the tubular body at different angles.

\* \* \* \* \*